United States Patent
Mumcu et al.

[11] Patent Number: 5,405,936
[45] Date of Patent: Apr. 11, 1995

[54] LIQUID-MELT ALIPHATIC DICARBOXYLIC ACIDS

[75] Inventors: Salih Mumcu, Marl; Franz-Erich Baumann, Dülmen, both of Germany

[73] Assignee: Huels Aktiengesellschaft, Marl, Germany

[21] Appl. No.: 205,731

[22] Filed: Mar. 4, 1994

[30] Foreign Application Priority Data

May 22, 1993 [DE] Germany .................. 43 17 189.3

[51] Int. Cl.⁶ .................... C08G 73/10; C08G 73/16; C07C 233/00
[52] U.S. Cl. .................... 528/310; 528/170; 528/183; 528/185; 528/188; 528/289; 528/322; 528/323; 528/353; 564/153; 564/160
[58] Field of Search ............... 528/170, 183, 185, 188, 528/289, 310, 322, 323, 353; 564/153, 160

[56] References Cited

U.S. PATENT DOCUMENTS

| | | | |
|---|---|---|---|
| 3,856,791 | 12/1974 | Daniher et al. | 564/160 |
| 3,910,847 | 10/1975 | Thompson | 564/160 |
| 3,969,253 | 7/1976 | Poklacki . | |
| 5,091,572 | 2/1992 | Speranza et al. | 564/139 |
| 5,097,070 | 3/1992 | Lin et al. | 564/153 |
| 5,138,097 | 8/1992 | Speranza et al. | 564/153 |
| 5,139,706 | 8/1992 | Speranza et al. | 252/548 |
| 5,324,812 | 6/1994 | Speranza et al. | 528/338 |

*Primary Examiner*—John Kight, III
*Assistant Examiner*—Shelley A. Dodson
*Attorney, Agent, or Firm*—Oblon, Spivak, McClelland, Maier, & Neustadt

[57] ABSTRACT

Liquid-melt aliphatic dicarboxylic acids tend to undergo undesirable discoloration during prolonged storage. The discoloration can be avoided by an addition of 0.1 to 3.0% by weight of a primary amine.

12 Claims, 1 Drawing Sheet

LIQUID-MELT ALIPHATIC DICARBOXYLIC ACIDS

BACKGROUND OF THE INVENTION

1. Field of the Invention

The invention relates to liquid-melt aliphatic dicarboxylic acids having 8 to 18 C atoms in the carbon skeleton.

2. Discussion of the Background

Aliphatic dicarboxylic acids are widely used in a variety of applications. For example, they can be used as a raw material for the preparation of polyamides. An inexpensive preparation of polyamides starts from molten diamine and dicarboxylic acid. In this process, the components are melted, mixed and subjected to polycondensation in the melt. In practice, the disadvantage of the process is that the dicarboxylic acid can be melted only immediately before use, since it discolors severely in the molten state during prolonged storage. This discoloration is then transferred to the condensed polyamide. Such a discolored product is not accepted by the market.

To overcome this problem, the polycondensation is instead carried out in the aqueous phase. This process requires that large amounts of water must be heated and evaporated off on an industrial scale. Accordingly, aqueous phase polycondensation is not economically advantageous.

It is consequently desirable to discover routes for carrying out the polycondensation in the melt.

SUMMARY OF THE INVENTION

Accordingly, one object of the present invention is to provide a liquid-melt aliphatic dicarboxylic acid which shows no discoloration even after prolonged storage.

The present inventors have now surprisingly discovered that this object is achieved with a liquid-melt composition comprising a aliphatic dicarboxylic acid and 0.1 to 3.0% by weight of a primary amine, based on the amount of dicarboxylic acid. In a preferred embodiment, the composition comprises dicarboxylic acid and 0.5 to 2.0% by weight of primary amine. It is furthermore preferable to employ a dicarboxylic acid with a water content of 0 to $\leq 5\%$ by weight, based on its total weight.

DETAILED DISCUSSION OF THE PREFERRED EMBODIMENTS

Figure 1:
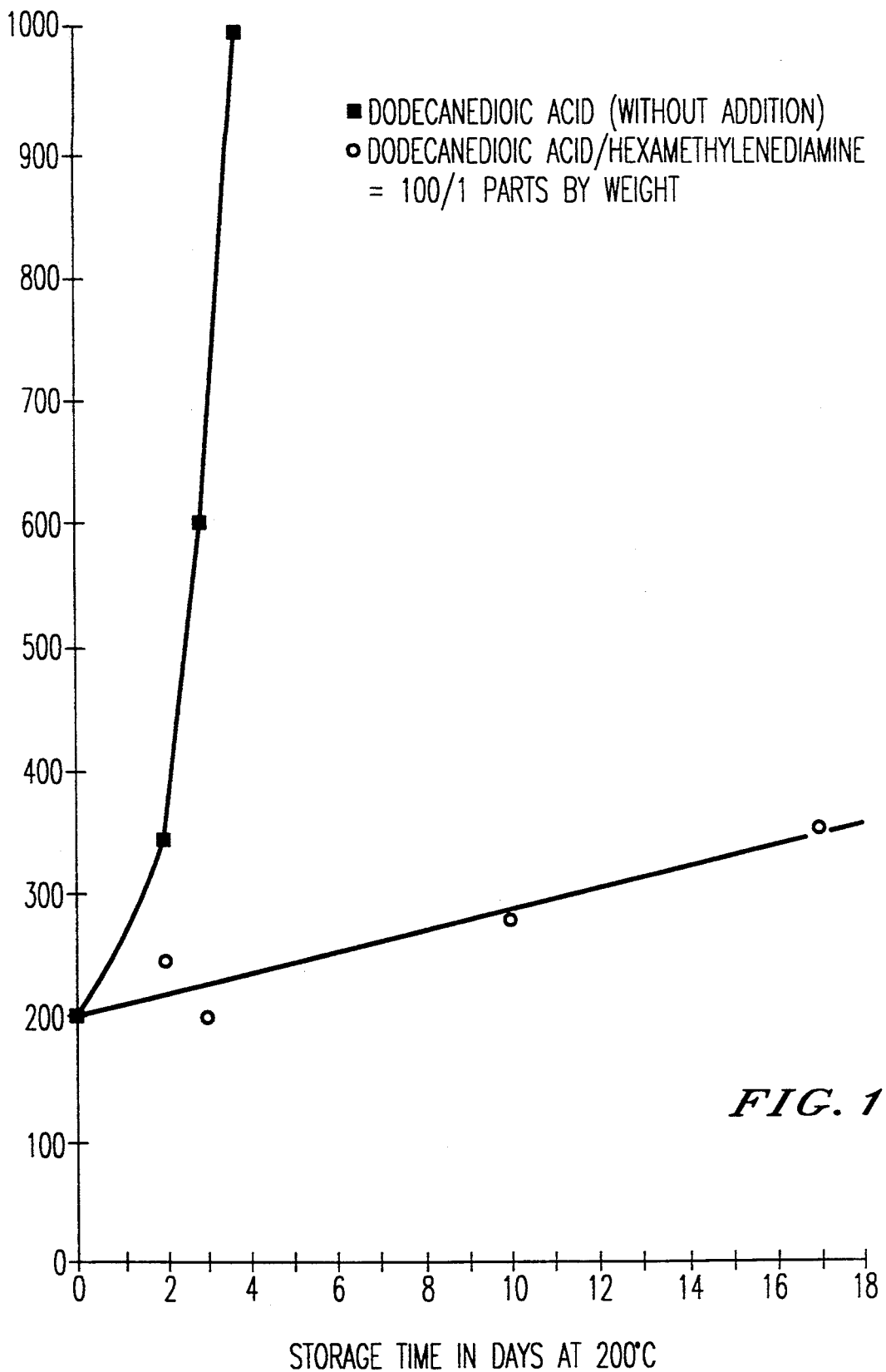
FIG. 1 illustrates the change in color over time of (1) a composition in accordance with the present invention as described in Example 1 and (2) a composition in accordance with the prior art as described in Example A.

Suitable primary amines useful in accordance with the present invention are those which have an aliphatic, cycloaliphatic, heterocyclic or araliphatic carbon skeleton having 4 to 20, preferably 6 to 13, C atoms. Aliphatic, cycloaliphatic or araliphatic primary amines are preferred.

Suitable primary monoamines include n-butylamine, n-hexylamine, n-dodecylamine, n-octadecylamine, cyclohexylamine and benzylamine. Mixtures of primary amines can also be used. Suitable di-primary amines include $\alpha,\omega$-hexamethylenediamine, $\alpha,\omega$-octa-methylenediamine, $\alpha,\omega$-decamethylenediamine, $\alpha,\omega$-dodecamethylenediamine, 1,4-bis (aminomethyl) cyclohexane, 4,4'-bis(aminocyclohexyl)methane, isophoronediamine, 2,2,4-trimethylhexamethylenediamine, 2,4,4-trimethylhexamethylenediamine, 2-methyl-pentmethylenediamine, 1,4-bis(aminomethyl)benzene, 1,3-bis(aminomethyl)benzene and mixtures thereof. Primary/secondary mixed diamines, such as triacetonediamine, can also be used.

The dicarboxylic acids preferably contain di-primary amines.

Suitable aliphatic dicarboxylic acids are those having 8 to 18, preferably 8 to 13, C atoms in the carbon skeleton. Suitable acids include subaric acid, azelaic acid, sebacic acid, undecanedioic acid, dodecanedioic acid and brassylic acid. Mixtures of dicarboxylic acids can also be employed.

The liquid-melt aliphatic dicarboxylic acids according to the invention are prepared according to conventional methods, for example, by melting the dicarboxylic acid in a stirred kettle. The primary amine is suitably added to the liquid-melt dicarboxylic acid and is distributed uniformly in the melt, while stirring. The preparation of the liquid-melt is understood to be not limited to this method. Any other industrially appropriate procedure can be used with the same success.

The liquid-melt aliphatic dicarboxylic acids according to the present invention have excellent color stability. Even after storage for several days, the dicarboxylic acid shows practically no discoloration. In contrast, a molten dicarboxylic acid which contains no amine is severely discolored to a yellow or brown after a few days.

It is imperative that the liquid melt dicarboxylic acids of the present invention be stored under an inert gas, for example nitrogen or argon.

The dicarboxylic acid according to the invention can be used for a variety of uses, in particular it can be used as a raw material for (co)polyamide, polyetheramide or polyether-ester-amide preparation. For this reason, it can contain the auxiliaries and additives customary for polyamide preparation, such as, for example, optical brighteners and polycondensation catalysts, in particular, acids derived from phosphorus. However, the invention is not limited to this field of use.

The production of (co)polyamides can be effected by condensing the liquid melt composition according to the invention with a diamine and optionally a lactam.

Correspondingly, polyetheramides can be produced by condensing the liquid melt composition according to the invention with a diamine, a polyether diamine and optionally a lactam, whereas polyether-ester-amides can be produced by condensing the liquid melt composition according to the invention with a diamine, a polyether diol end optionally a lactam (see, for instance, U.S. Pat. Nos. 4,207,410, 4,345,052, 4,345,064, 4,349,661, 4,429,081 and DE-A 30 06 961).

The determination of the color number in accordance with APHA is carried out in cells (height: 300 mm—diameter: 25 mm) in a methanolic dicarboxylic acid solution (20% strength by weight) in daylight. This solution being compared with aqueous solutions of $CoCl_2$ and $K_2PtCl_6$ in various concentrations as color standards (DIN 53 409).

The determination of the relative solution viscosity of the polyamides is carried out using a 0.5% strength by weight m-cresol solution at 25° C. (DIN 53 727/ISO 307).

To determine the amount of carboxyl end groups, 1 g of polyamide is dissolved in 50 ml of benzyl alcohol at 165° C. while covering with nitrogen. The solution time is not more than 20 minutes. The solution is titrated with a solution of KOH in ethylene glycol (0.05 mol of KOH/1) against phenolphthalein until the color changes.

To determine the amount of amino end groups, 1 g of polyamide is dissolved in 50 ml of m-cresol at 25° C. The solution is titrated potentiometrically with perchloric acid.

The determination of the melting points is carried out by means of DSC (ASTM D 34/8).

Having generally described this invention, a further understanding can be obtained by reference to certain specific examples which are provided herein for purposes of illustration only and are not intended to be limiting unless otherwise specified.

EXAMPLES

The examples identified with letters are not according to the invention.

Example 1

2 kg of anhydrous dodecanedioic acid and 20 g of n-hexa-methylenediamine were melted under deoxonitrogen in a 5 l stirred autoclave and stored at 200° C. for 3 weeks. Samples were removed via the bottom valve at regular intervals, and the APHA number of these was determined. The results obtained are shown in the FIG. 1.

Example A

Example 1 was repeated—but with the exception that no diamine was added. The results obtained are shown in the FIG. 1.

Example 2

664.6 kg of dodecanedioic acid (DDA) was mixed together with 6.71 kg of hexamethylenediamine (HMD), melted and stored at 165° C. in a tank (capacity: 1 m³). 16.269 kg of 85% strength by weight anhydrous HMD=140.0 mol) were melted in a second tank while stirring with an anchor stirrer in the course of 14 hours and forced into a polycondensation tank. 33.567 kg of liquid-melt product comprising 33.231 kg of DDA (=144.3 mol) and 0.335 kg of HMD 2.886 mol) were fed from the 1 m3 tank to the polycondensation tank by a metering pump. A mixing temperature of 193° C. was established in the polycondensation tank. Under the autogenous pressure, the melt was heated up to 245° C. (22 bar) and left thus for one hour. Thereafter, it was heated up to 265° C. (normal pressure) with continuous letting down. A stream of $N_2$ was then passed over for 20 minutes. The melt was discharged from the polycondensation tank as a strand and was granulated. 43.0 kg of colorless granules were obtained.

The granules had the following properties:

$\eta_{rel}$=1.67
$T_m$=219° C.
[COOH]=122 meq/kg
[$NH_2$]=31 meq/kg

Extruded film (100 µm thick): translucent, colorless, smooth

Example 3

Example 2 was repeated with the same dodecanedioic acid which had been stored in the liquid-melt state for 5 days. Colorless granules with comparable properties of the film produced therefrom were obtained.

Example B 500 kg of DDA were melted under nitrogen and stored at 165° C. in a tank (1 m³) with an anchor stirrer without addition of HMD. 19.728 kg of 85% strength by weight HMD (144.30 mol) was preheated to 70° C. in the course of 14 hours in a second tank, while stirring. During this operation, 33.563 kg of fused DDA (=145.88 mol) was forced from the reservoir tank into the polycondensation tank and the melt was preheated to 245° C. HMD was then forced out of the second tank. A mixing temperature of 193° C. was established in the polycondensation tank. Under the autogenous pressure, the mixture was heated to 245° C. (22 bar), while stirring; the pressure was maintained for one hour. Thereafter, the mixture was heated up to 265° C. (normal pressure) while continuously letting down. A stream of $N_2$ was subsequently passed over in the course of 20 minutes. The product was then discharged and granulated. 43.2 kg of yellow granules were obtained.

The granules had the following properties:

$\eta_{rel}$=1.63
$T_m$=219° C.
[COOH]=124 meg/kg
[$NH_2$]=38 meg/kg

Extruded film (100 µm thick): translucent, discolored yellow, smooth

Example C

Example B was repeated with the same dodecanedioic acid which had been stored in the liquid-melt state for two days. Severely yellowed granules with the following properties were obtained:

$\eta_{rel}$=1.65
$T_m$=218° C.
[COOH]=116 meq/kg
[$NH_2$]=33 meq/kg

Extruded film (100 µm thick): translucent, severely discolored yellow, streaks

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A liquid-melt composition comprising an aliphatic dicarboxylic acid having 8 to 18 C atoms and 0.1 to 3.0% by weight, based on the weight of said dicarboxylic acid, of a primary amine.

2. The liquid-melt composition according to claim 1, wherein said aliphatic dicarboxylic acid has 8 to 13 C atoms.

3. The liquid-melt composition according to claim 1, wherein said aliphatic dicarboxylic acid is suberic acid, sebacic acid, dodecanedioic acid, azelaic acid or brassylic acid.

4. The liquid-melt composition according to claim 1, wherein said composition comprises of from 0.5 to 2.0% by weight, based on the weight of said dicarboxylic acid, of a primary amine.

5. The liquid-melt composition according to claim 1, wherein said primary amine is a primary diamine.

6. The liquid-melt composition according to claim 1, wherein said primary amine is n-butylamine, n-hexylamine, n-dodecylamine, n-octadecylamine, cyclohexylamine or benzylamine.

7. The liquid-melt composition according to claim 1, wherein said primary amine is α,ω-hexamethylenediamine, α,ω-octamethylenediamine, α,ω-decamethylenediamine, α,ω-dodecamethylenediamine, 1,4-bis(aminomethyl)cyclohexane, 4,4'-bis(aminocyclohexyl)methane, isophoronediamine, triacetonediamine, 2,2,4-trimethylhexamethylenediamine, 2,4,4-trimethylhexamethylenediamine, 2-methyl-pentamethylenediamine, 1,4-bis(aminomethyl)benzene or 1,3-bis(aminomethyl)benzene.

8. A process for the preparation of (co)polyamides, comprising: condensing a liquid-merit composition comprising an aliphatic dicarboxylic acid having 8 to 18 C atoms and 0.1 to 3.0% by weight, based on the weight of said dicarboxylic acid, of a primary amine with a diamine and optionally a lactam.

9. A process for the preparation of polyetheramides comprising: condensing a liquid-melt composition comprising an aliphatic dicarboxylic acid having 8 to 18 C atoms and 0.1 to 3.0% by weight, based on the weight of said dicarboxylic acid, of a primary amine with a diamime, a polyether diamine and optionally a lactam.

10. A process for the preparation of polyether-esteramides comprising: condensing a liquid-melt composition comprising an aliphatic dicarboxylic acid having 8 to 18 C atoms and 0.1 to 3.0% by weight, based on the weight of said dicarboxylic acid, of a primary amine with a diamime, a polyether diol and optionally a lactam.

11. A process for storing a aliphatic dicarboxylic acid comprising:
   melting said aliphatic dicarboxylic acid in the presence of 0.1 to 3.0% by-weight, based on the total weight of said dicarboxylic acid, of a primary amine,
   storing said liquid-melt composition under an inert atmosphere.

12. The process according to claim 11, wherein said inert atmosphere is nitrogen.

* * * * *